(12) United States Patent
Kennedy et al.

(10) Patent No.: US 11,443,464 B2
(45) Date of Patent: Sep. 13, 2022

(54) METHOD OF VOLUMETRIC IMAGING OF A SAMPLE

(71) Applicant: OncoRes Medical Pty Ltd, Nedlands (AU)

(72) Inventors: Brendan Kennedy, Crawley (AU); Brooke Krajancich, Crawley (AU); Qi Fang, Crawley (AU); Andrea Curatolo, Crawley (AU)

(73) Assignee: OncoRes Medical Pty Ltd, Nedlands (AU)

( * ) Notice: Subject to any disclaimer, the term of this patent is extended or adjusted under 35 U.S.C. 154(b) by 43 days.

(21) Appl. No.: 16/754,269

(22) PCT Filed: Sep. 18, 2018

(86) PCT No.: PCT/AU2018/051024
§ 371 (c)(1),
(2) Date: Apr. 7, 2020

(87) PCT Pub. No.: WO2019/071295
PCT Pub. Date: Apr. 18, 2019

(65) Prior Publication Data
US 2020/0273216 A1    Aug. 27, 2020

(30) Foreign Application Priority Data
Oct. 11, 2017   (AU) .................................. 2017904109

(51) Int. Cl.
*G06T 11/00*      (2006.01)
*G06T 7/50*       (2017.01)
(Continued)

(52) U.S. Cl.
CPC .......... *G06T 11/008* (2013.01); *A61B 5/0066* (2013.01); *G06T 5/00* (2013.01);
(Continued)

(58) Field of Classification Search
CPC ....... G06T 11/008; G06T 7/0012; G06T 7/50; G06T 2207/10028; G06T 2207/10101;
(Continued)

(56) References Cited

U.S. PATENT DOCUMENTS 9,734,589 B2 *  8/2017  Yu ........................... G06T 7/292
2006/0256913 A1  11/2006  Roberts et al.
(Continued)

FOREIGN PATENT DOCUMENTS

JP    2007130403 A   5/2007
WO    2009149131 A1  12/2009
WO    2010101162     9/2010

OTHER PUBLICATIONS

International Search Report for Application No. PCT/AU2018/051024 dated Oct. 30, 2018 (3 pages).
(Continued)

*Primary Examiner* — Jon Chang
(74) *Attorney, Agent, or Firm* — Michael Best & Friedrich LLP (57) ABSTRACT

The present disclosure provides a method of volumetric imaging of a sample. The method comprises providing a plurality of depth images of a region of interest of the sample using a volumetric imaging system. The region of interest is below a surface area of interest of the sample. Each depth image is associated with a layer or slice of the region of interest and the plurality of depth images together forming a volumetric image of the region of interest. The method further comprises providing a surface image of the surface area of interest of the sample and identifying a surface image property of a surface feature of the surface area of interest. The method also comprises processing the plurality of depth images of the region of interest using the surface image (Continued)

property of the surface feature to improve a property of the depth images of the region of interest.

17 Claims, 8 Drawing Sheets

(51) Int. Cl.
  *G06T 7/00* (2017.01)
  *G06T 7/55* (2017.01)
  *G06T 7/90* (2017.01)
  *G06T 5/00* (2006.01)
  *A61B 90/00* (2016.01)
  *A61B 5/00* (2006.01)
  *A61B 1/267* (2006.01)
(52) U.S. Cl.
  CPC .............. *G06T 7/0012* (2013.01); *G06T 7/50* (2017.01); *G06T 7/55* (2017.01); *G06T 7/90* (2017.01); *A61B 1/267* (2013.01); *A61B 2090/363* (2016.02); *G06T 2207/10028* (2013.01); *G06T 2207/10101* (2013.01); *G06T 2207/20172* (2013.01); *G06T 2207/30004* (2013.01)
(58) Field of Classification Search
  CPC . G06T 2207/30004; G06T 7/97; G06T 7/248; G06T 7/337; G06T 7/55; G06T 7/90; G06T 2207/10024; G06T 2207/20172; G06T 2207/20224; G06T 5/00; A61B 1/000094; A61B 5/0066; A61B 5/0073; A61B 1/267; A61B 5/0037; A61B 1/04; A61B 1/0638; A61B 8/085; A61B 8/0858; A61B 8/483; A61B 2090/363; G06V 10/56
  See application file for complete search history.

(56) References Cited

U.S. PATENT DOCUMENTS

| | | |
|---|---|---|
| 2011/0267340 A1 | 11/2011 | Kraus et al. |
| 2015/0265220 A1* | 9/2015 | Ernst ..................... G06T 7/292 600/411 |
| 2016/0040977 A1 | 2/2016 | An et al. |
| 2016/0206272 A1 | 7/2016 | Kyriakou |
| 2019/0046276 A1* | 2/2019 | Inglese ................. A61B 34/20 |

OTHER PUBLICATIONS

Kennedy et al., "Optical coherence micro-elastography: mechanical-contrast imaging of tissue microstructure," Biomedical Optics Express, vol. 5, No. 7, published Jun. 9, 2014, 12 pages.
Liew et al., "Motion correction of in vivo three-dimensional optical coherence tomography of human skin using a fiducial marker," Biomedical Optics Express, vol. 3, No. 8, published Jun. 29, 2012, 13 pages.
European Patent Office Extended Search Report for Application No. 18866088.0 dated May 10, 2021 (8 pages).

* cited by examiner

METHOD OF VOLUMETRIC IMAGING OF A SAMPLE

FIELD OF THE INVENTION

The present invention broadly relates to a method of volumetric imaging of a sample, and relates particularly, though not exclusively, to optical coherence tomography (OCT).

BACKGROUND

Optical coherence tomography (OCT) is a well-known imaging technique that utilises light to obtain high resolution images of a surface of an object. Depending on the object, the light will also penetrate beneath a surface of the object to some degree, and accordingly, an OCT image can capture depth information of the object. For example, light from an OCT imaging system may penetrate 2-3 mm into biological tissue.

An OCT image is constructed by measuring light back-scattered from a sample over a relatively narrow range of wavelengths. Because of this, an OCT image does not intrinsically contain any information regarding the colour of the sample taken.

An OCT image of a surface of a sample is also typically acquired by linear scanning light across the surface of the sample. This can be done with a hand-held OCT probe, for example, to acquire an image of an object. The OCT probe needs to be stationary relative to the object (such as a human body) in order to obtain high resolution OCT images. However, it is possible for the object and the OCT probe to move relative to each other during scanning. This motion artefact can cause skewed OCT images having reduced resolution.

SUMMARY OF THE INVENTION

In a first aspect of the present invention there is provided a method of volumetric imaging of a sample, the method comprising the steps of:
  providing a plurality of depth images of a region of interest of the sample using a volumetric imaging system, the region of interest being below a surface area of interest of the sample, each depth image being associated with a layer or slice of the region of interest and the plurality of depth images together forming a volumetric image of the region of interest;
  providing a surface image of the surface area of interest of the sample;
  identifying a surface image property of a surface feature of the surface area of interest; and
  processing the plurality of depth images of the region of interest using the surface image property of the surface feature to improve a property of the depth images of the region of interest.

In a first embodiment of the present invention the surface image property is a visible property of a surface portion, such as a colour (e.g. an RGB colour) of the surface portion. In this embodiment the method comprises:
  identifying the visible property of the surface feature, such as the colour of the surface portion; and
  identifying a portion of at least some of the depth images of the region of interest, the identified portion corresponding to, and/or belonging to the same volume type as, the surface portion;
  associating the identified portion of at least some of the depth images with the surface image property of the surface portion, such as the colour; and
  processing the plurality of depth images of the region of interest using the surface image property to improve a property, such as image contrast, of the depth images of the region of interest.

The surface image may be taken using a different imaging system to the volumetric imaging system. For example, the surface image may be a photograph of the sample acquired using a camera. In another example, the surface image may be a micrograph of a histological sample.

It will be appreciated that if the surface image is a grayscale image, the surface image property may be a grayscale value of the surface image.

For example, the sample may be biological tissue and the volume type may be a blood vessel, an organ portion or another portion typically having a tissue property that is different from a tissue property of surrounding tissue.

The method may comprise displaying the volumetric image with the same volume type having the property, such as the colour.

The imaging system may for example be an OCT imaging system.

The method may comprise determining a change in attenuation of an optical signal, such as an OCT signal, as a function of depth to determine a cross-sectional shape or depth extent of the identified portion.

The sample may be biological tissue and the method may be conducted in-vivo or ex-vivo. For example, the method may be performed through an endoscope, such as a bronchoscope incorporated with an OCT imaging system and a digital camera.

In a second embodiment of the present invention the method comprises providing a series of surface images of the surface area of interest during movement of the volumetric imaging system and the surface area or volume of interest relative to each other. For example, the volumetric imaging system may comprise a hand-held probe and the movement may be unintentional and may be caused by a user and/or a patient. Each surface image may have a surface feature having a property, which in this embodiment is a spatial position. The method may comprise identifying a change in the spatial position of the surface feature of each surface image and processing the plurality of depth images of the region of interest using the identified change of the spatial position to obtain a plurality of depth images of the region that are at least largely corrected for an impact of the movement of the volumetric imaging system and the surface area of the region of interest relative to each other.

The movement of the volumetric imaging system and the surface area of the sample of interest relative to each other may be a movement of the volumetric imaging system along the surface area of interest.

Processing the plurality of depth images of the region of interest using the identified change in the spatial position of the surface feature may comprise processing the plurality of depth images to correct for at least 1, 2, 3 or more degrees of freedom.

For example, there may be 6 degrees of freedom, corresponding to: translational movement in an x, y or z direction, and rotational movement such as pitch, roll or yaw.

The step of processing the plurality of depth images may comprise correcting for deformation in the surface plane. For example, if a motion artefact causes a shear force to deform surface features relative to each other, the processing step could detect this and correct for it in the OCT volume.

The volumetric imaging system may for example be an OCT imaging system comprising a scanning mirror. In this embodiment the scanning mirror may be arranged for motion correction using a suitable suspension (which may be MEMS-based) with actuators.

In a second aspect of the present invention there is provided a method of volumetric imaging of a sample, the method comprising the steps of:

providing a plurality of depth images using a volumetric imaging system during movement of a volumetric imaging system and the sample relative to each other, the volumetric imaging system being arranged for mechanical correction of the relative motion between the imaging system and the sample, each depth image being associated with a layer or slice of the region of interest and the plurality of depth images together forming a volumetric image of the region of interest;

providing a plurality of surface images during movement of the volumetric imaging system and the sample relative to each other;

identifying changes in spatial position of surface features of the surface images to obtain positional information; and controlling the volumetric imaging system to correct for an impact of the movement of the volumetric imaging system and the sample relative to each other using the obtained positional information.

The volumetric imaging system may be arranged such that the movement correction can be performed mechanically using a suitable control system with a feedback loop. The movement correction may be performed substantially automatically and substantially in real time.

In one specific embodiment the region of interest below the surface area of interest has a size that is limited by a capability or scanning range of a volumetric imaging system. For example, a selected volumetric imaging system may be arranged to obtain the depth images below a surface area A (such as 10×10 mm$^2$ for example). In order to obtain larger volumetric images (corresponding to a region below for example 2A or any other larger area size), the volumetric imaging system and the sample are moved relative to each other by corresponding distance. The movement may be performed manually and may or may not be an accurate movement (such as a movement along a straight line and covering a distance of A using the above example). The method comprises providing a plurality of surface images during movement of the volumetric imaging system and the sample relative to each other. The method further comprises identifying changes in the spatial position of surface features of the surface image and processing the plurality of depth images using the identified changes of the spatial positions to identify corrected positions of the depth images. In this case typically at least one surface image is provided for each depth image during movement of the volumetric imaging system and the sample relative to each other. The method may then comprise generating at least one volumetric image (extended to span for example 2A) using the obtained depth images and the identified corrected spatial positions of each depth image.

In one specific example the volumetric imaging system may have a scanning range A and the sample and the volumetric scanning system may be moved relative to each other such that a region B of the sample is scanned and the region B has a surface extension that is larger than the scanning range A and the at least one volumetric image is an image corresponding to the region B.

The sample may be biological tissue and the method may be conducted in-vivo or ex-vivo. For example, the method may be performed through an endoscope, such as a bronchoscope incorporated with an OCT imaging system and a digital camera.

The imaging system may for example be an OCT imaging system.

The method may comprise characterising the micro-elastography of the region of interest.

The sample may be biological tissue and the method may be conducted in-vivo or ex-vivo. For example, the method may be performed this through an endoscope, such as a bronchoscope incorporated with an OCT imaging system and a digital camera.

The volumetric imaging system may comprise a layer having known mechanical properties and incorporating a fiducial marker, the method further comprising:

positioning the layer on the surface area of interest;
applying a load to the region of interest and through the layer;
detecting a deformation of the layer in response to the applied load; and
using the fiducial marker for correcting for motion artefacts.

The layer may comprise a layered structure within which the fiducial marker is positioned. The layered structure may comprise layers having differing stiffness and the fiducial marker may be embedding in a layer having a stiffness that is greater than that of another layer of the layered structure. The layer in which the fiducial marker is positioned may in use be located between the other layer having the lower stiffness and the region of interest. The layered structure may also comprise a contact layer that has a stiffness that is lower than that of the layer in which the fiducial marker is embedded and in use the layer in which the fiducial marker is embedded may be positioned between two layers having the lower stiffness. The layers between which the layer in which the fiducial marker is embedded is sandwiched may have a stiffness similar to that of the region of interest.

The step of providing a plurality of depth images of a region of interest comprises OCT imaging. Further, the step of detecting a deformation of the layer in response to an applied load comprises OCT imaging of interfaces of the layer.

DETAILED DESCRIPTION OF SPECIFIC EMBODIMENTS

In general terms, embodiments of a method according to the invention involve improving, correcting or otherwise modifying a volumetric image of a sample using information derived from a surface image of a surface of the sample.

The volumetric image is obtained using a volumetric imaging system, which acquires a plurality of depth images. In particular, each depth image is associated with a layer or slice of a region of interest of the sample, and the plurality of depth images together form the volumetric image of the region of interest.

The surface image of the sample is preferably obtained using a different imaging technique. For example, the surface image may be a photograph of the sample acquired using a camera, or a micrograph of a sample taken using a microscope, while the depth image may be an OCT image of the sample acquired using an OCT imaging system.

The method further involves identifying a surface image property of a feature or features of the surface image that has been obtained. The surface image property may for example be a visible property of the surface feature(s), such as an RGB colour. Alternatively, the surface image property may be a spatial position of the surface feature(s). The method then comprises processing the plurality of depth images using the surface image property to improve a property of the depth images of the region of interest.

Figure 1:
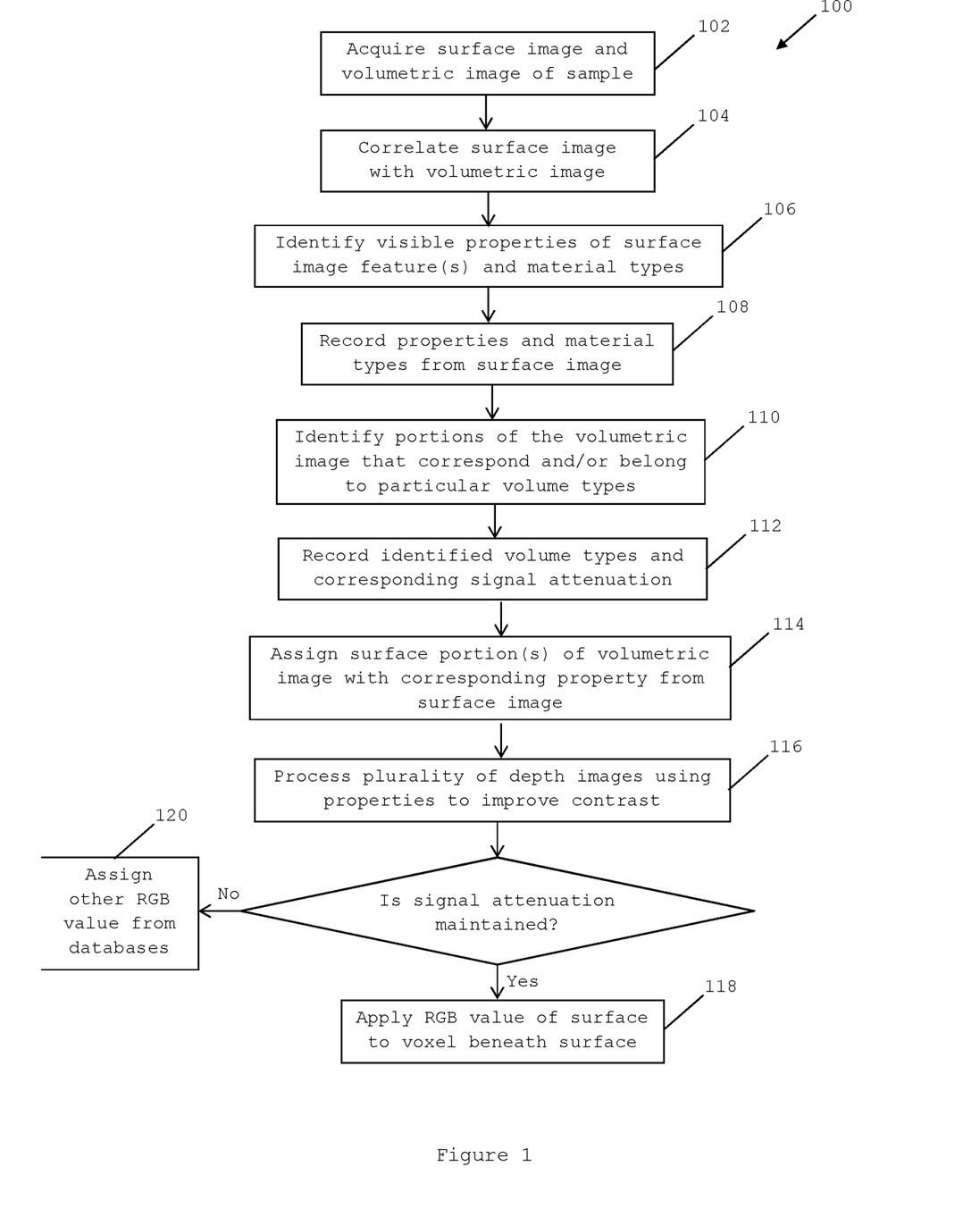
FIG. 1 is a flow diagram of a method according to an embodiment of the present invention.

FIG. 1 is a flow diagram illustrating a method 100 according to a first embodiment of the invention. In general terms, the method 100 can assist in obtaining a coloured volumetric image by associating various portions of the volumetric image with corresponding coloured portions of the surface image of the sample.

Figure 2:
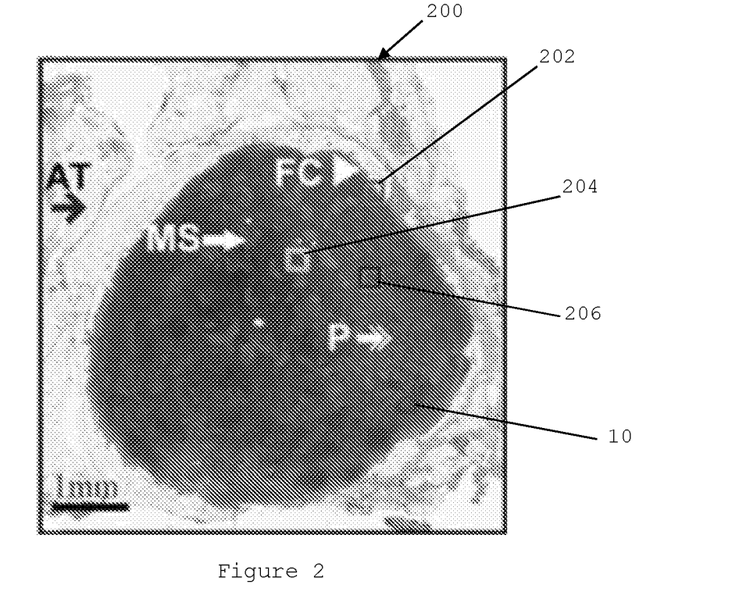
FIG. 2 is a surface image captured according to an embodiment of the present invention.
Figure 3:
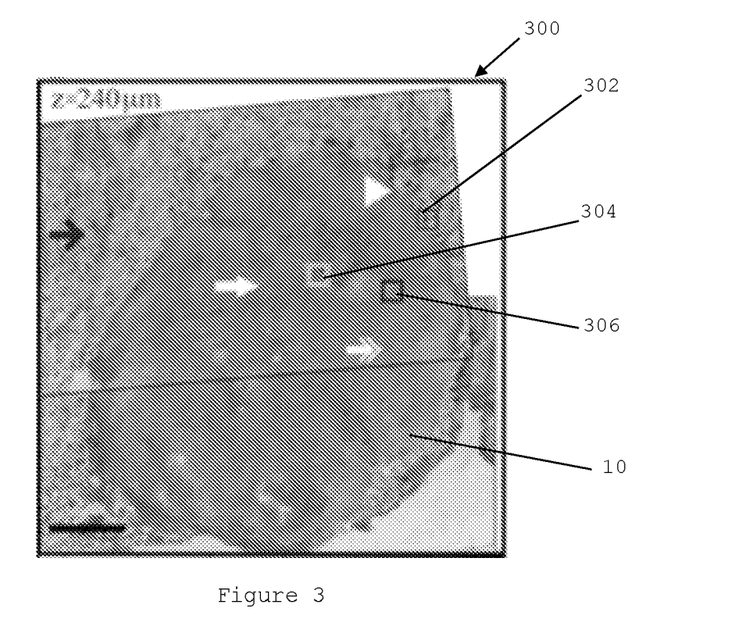
FIG. 3 is a volumetric image captured using a volumetric imaging system according to an embodiment of the present invention.

The method 100 involves step 102 of acquiring the surface image and the volumetric image of the sample. FIG. 2 is a surface image 200 in the form of a colour micrograph of a biological sample 10 that has been histologically prepared. The histology image 200 has been acquired by excising biological tissue, treating the tissue (e.g. by applying a fixative), staining, sectioning and mounting on a slide. However, it will be appreciated that the micrograph of the histological image is only an example. Those skilled in the art will appreciate that other types of surface images may be used and may even be preferable, such as a photograph of the sample taken in vivo. FIG. 3 shows an example of a volumetric image 300 of the biological sample 10 obtained using OCT, at a depth of 240 µm.

The volumetric image 300 and the surface image 200 of the sample are then correlated 104 with each other. This involves associating a surface portion of each depth image, i.e. each image slice, of the volumetric image 300, with a corresponding surface portion of the surface image 200.

The method 100 then involves identifying 106 a visible property of one or more surface features of the surface image and corresponding material types, such as tissue types. In this example, the visible property is an RGB colour of the surface features. In particular, identifying 106 the RGB colour involves inspecting the surface image 200 to identify differently coloured portions of the image 200, such as the portions 202, 204 and 206. This can be done by visual inspection or using a suitable computer program if the image 200 is a digital image. Differently coloured portions of the sample are usually indicative of different biological tissue types, such as a muscular tissue, fatty tissue, a tumour or blood vessel in the case of a biological sample. The differently coloured portions can thus be associated with a particular tissue type.

The RGB values of the differently coloured portions and the corresponding tissue type are then recorded 108 in a database, such as a data storage medium of a computer device. It will be appreciated that the database may already have existing RGB values and corresponding tissue types recorded, for example, from previous surface images. Entries in the database are preferably acquired under the same controlled imaging conditions, such as exposure time, lighting conditions etc.

The method 100 also involves identifying 110 portions of the volumetric image 300 that correspond and/or belong to particular volume types. In this example, the volume type is a tissue type. This can be done by measuring an attenuation of the OCT signal with depth. In particular, the OCT image 300 in FIG. 3 can be divided into voxels, i.e. elements of volume. For each voxel, a signal attenuation factor can be estimated based on the decay in OCT signal backscattered in surrounding voxels when acquiring the OCT image.

Figure 4A:
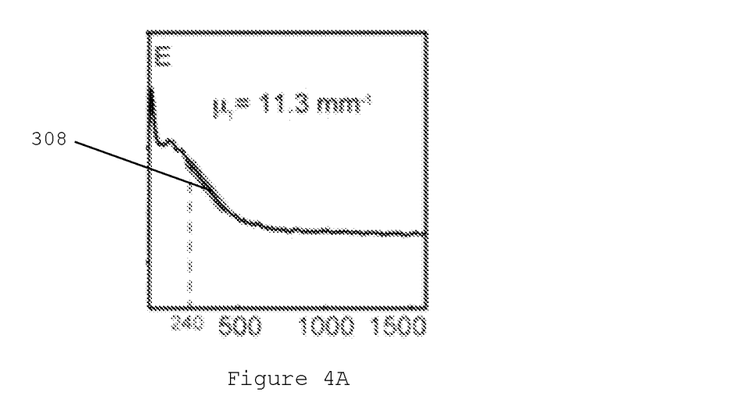
FIGS. 4A to 4C are logarithmic plots of signal attenuation used according to an embodiment of the present invention.
Figure 4B:
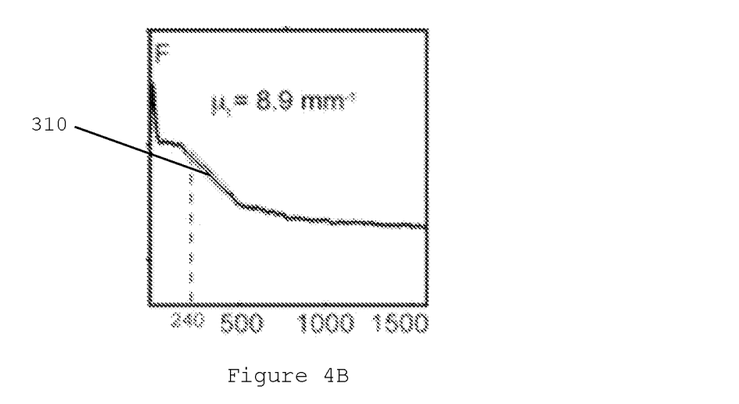
Figure 4C:
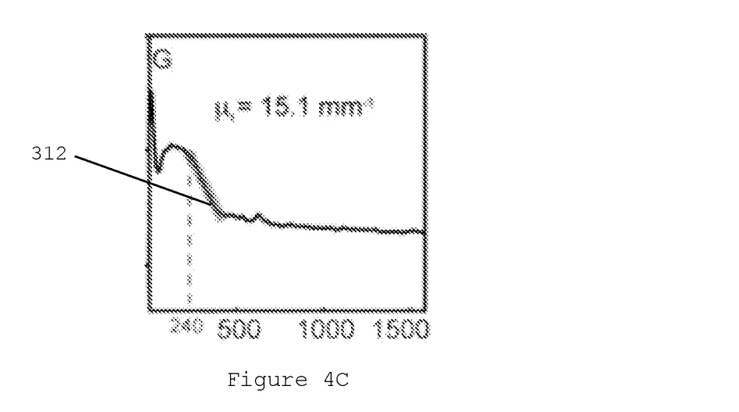

For example, FIG. 4A shows a logarithmic plot of OCT signal attenuation as a function of depth (µm) at the position 302 corresponding in the OCT image corresponding to the position 202 of the surface image. Similarly, FIG. 4B shows a plot of signal attenuation at the position 304 of the OCT image 300 corresponding to the position 204 of the surface image 200, and FIG. 4C shows a plot of signal attenuation at the position 306 of the OCT image 300 corresponding to the position 206 of the surface image 200. In a given tissue type, the slope of attenuation is substantially constant with depth. Therefore, when the plot changes in slope, it can generally be said that a different tissue type is present at a respective depth.

In each of FIGS. 4A to 4C, a substantially constant slope 308, 310 and 312 is identified, which corresponds to a particular tissue type at the positions 302, 304 and 306, respectively. The portions of the plots before and after each slope 308, 310 and 312 are likely to be indicative of a different tissue type at a respective depth to the tissue type associated with the plot. Moreover, it can be said that the tissue types at positions 302, 304 and 306 are likely to be different to each other, since they have different signal attenuation slopes. It is noted that signal attenuation is a more intrinsic measure of tissue type than the amount of backscattered light, as the latter depends on the cumulative reduction of light intensity occurred from tissues at all depths before the one of interest. In FIGS. 4A to 4C, $\mu_t$ is the attenuation coefficient and is measured as the slope of reflectance with respect to depth. The attenuation coefficient can be derived, for example, according to the technique described in "Fibrin phantom for use in optical coherence tomography" (B. F. Kennedy and P. Rigby 2010, Journal of Biomedical Optics, Volume 15, Number 3, p. 2).

The identified tissue types and corresponding signal attenuation values associated with the OCT image 300 are then recorded 112 in a database, such as a data storage medium of a computer device. It will be appreciated that the database may already have existing RGB values and corresponding tissue types recorded, for example, from previous surface images.

Then, RGB values from the surface image are assigned 114 to a surface portion of the volumetric images. In particular, surface portions (or other portions of a reference plane) of each voxel at the surface (or reference plane) of the volumetric image 300 are each associated with a corresponding RGB value derived from the surface image 200. Specifically, a corresponding RGB colour can be applied to the OCT image 300 such that the surface level of the OCT image 300 is coloured with substantially realistic colourings. Hence, RGB values corresponding to the structure at the tissue surface are used to colour-code the OCT image 300.

However, it will be appreciated that since the OCT image 300 is constructed by depth images or 2D cross-sectional slices, such colour-coding can also be applied at different depths of the OCT image 200. Therefore, the method 100 involves further processing 116 the plurality of depth images using the RGB colours to improve a property, such as image contrast, of the depth images.

In particular, according to this embodiment, for each voxel below the OCT image surface or reference plane, if the signal attenuation is maintained (i.e. still constant) compared to that of surface or reference plane, the RGB value assigned to the surface or reference plane will be applied 118 to that voxel.

If not, another RGB value will be assigned 120 to that voxel, which may be derived from the RGB database and signal attenuation database referred to in steps 108 and 112. For example, if the signal attenuation for that voxel is determined, the signal attenuation database may have a record of what tissue type the signal attenuation corresponds to. The identified tissue type may then have a corresponding RGB value in the RGB database.

Figure 5:
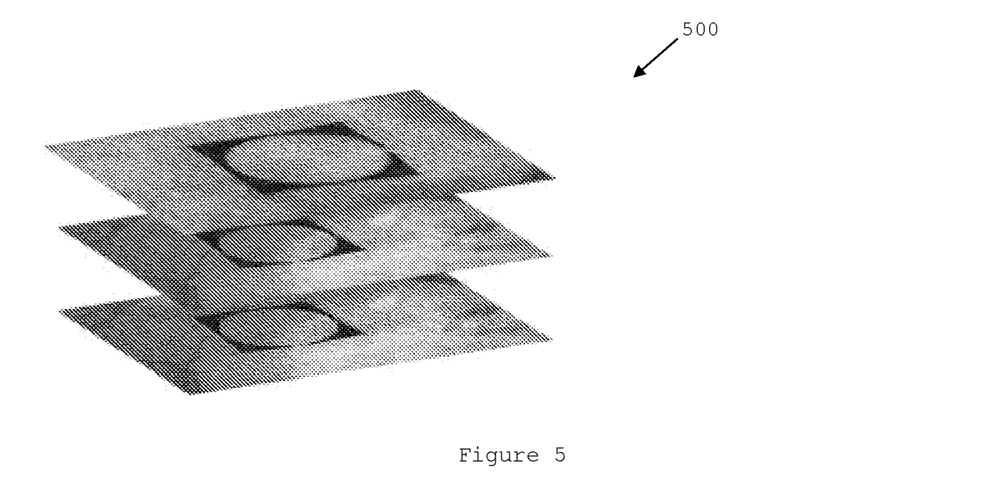
FIG. 5 is a coloured volumetric image obtained as a result of an embodiment of the present invention.

As a result of the method 100, coloured OCT images 500 at different depths can be obtained, as shown in FIG. 5.

It will be appreciated that embodiments of the method 100 described above may provide the advantage of obtaining a more visually-appealing volumetric image, for example to clinicians, to facilitate rapid interpretation of images.

It will also be appreciated that not only has the OCT image 300 been transformed into a colour image, the contrast of the OCT image 300 has been improved such that there is now improved delineation of different tissue types in the OCT image 300.

An algorithm or appropriate computer programming software can be used to perform the method 600. Also, according to an alternative embodiment, if the surface image is a grayscale image, the surface image property may be a grayscale value of the surface image.

Figure 6:
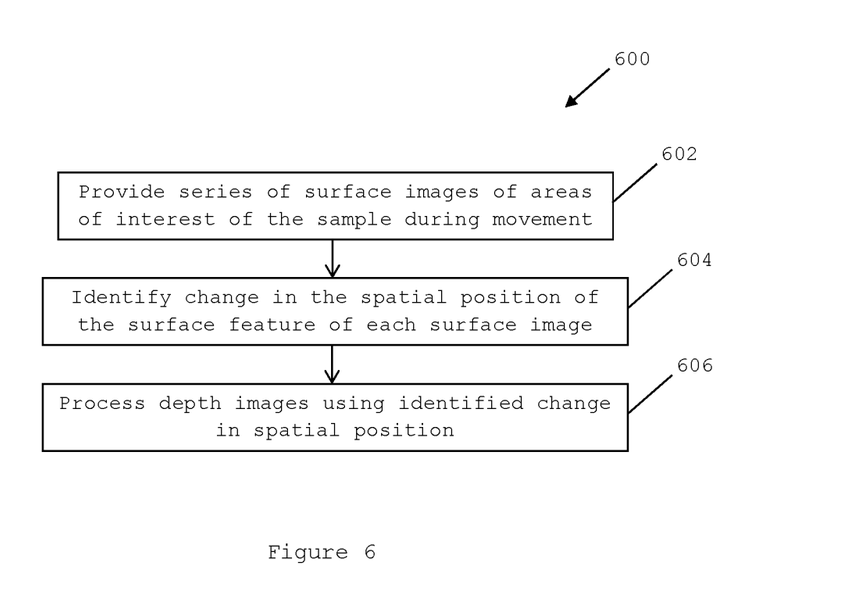
FIG. 6 is a flow diagram of a method according to another embodiment of the present invention.

FIG. 6 is a flow diagram illustrating a method 600 according to a second embodiment of the invention. In general terms, the method 600 can assist in providing motion correction of volumetric images that have been obtained by some form of scanning. Therefore, the property of the surface feature used to improve the volumetric image is, in this embodiment, a spatial position.

To provide context, it is noted that surface images such as digital photographs are acquired in the plane orthogonal to the acquisition of 2D cross-sectional scans, such as scans that make up an OCT image. As a result, photographs provide a snapshot of the surface of a sample. In contrast, volumetric imaging techniques such as OCT or micro-elastography can only provide a view of the tissue surface once a 3D scan (i.e. a series of depth images, or 2D cross-sectional scans across the sample surface) has been acquired. However, a position of the sample may drift or change during the 2D cross-sectional scans, which may introduce motion artefact and result in a skewed or distorted image. This may occur for example when the sample is a portion of a patient's body, and the patient moves during the scan or in a handheld probe if the user's hand moves during the scan.

To potentially address the issue of motion artefact described above, the method 600 comprises providing 602 a series of surface images of areas of interest of the sample during movement of the volumetric imaging system relative to the sample. For the avoidance of doubt, such movement can be movement of the imaging system, with respect to the sample, or movement of the sample with respect to the imaging system. Therefore, according to this embodiment, when the imaging system takes a linear scan of the sample to obtain a 2D cross-section, at least one surface image of the sample is also acquired, which will be associated with the particular line scan taken. However, it will be appreciated that in alternative embodiments, greater than or less than one surface image of the sample per B-scan line can be taken. For example, one surface image every two or more B-scan lines can be taken, and for the B-scan lines that do not have a corresponding surface image, a measure of shift (such as the transformation matrix described below) for those B-scan lines can be interpolated.

Figure 7:
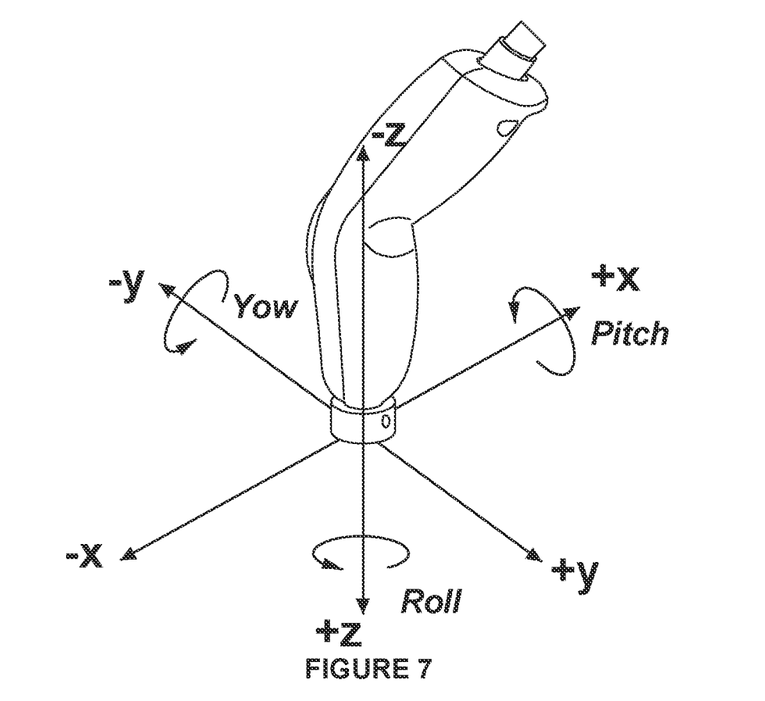
FIG. 7 shows an OCT probe for use according to an embodiment of the present invention.

In this example, the volumetric imaging system comprises a hand-held scanning probe capable of acquiring at least OCT images, such as a probe 12 shown in FIG. 7. Also shown in FIG. 7 are six degrees of movement that can be experienced by a hand-held probe during a volumetric acquisition: translational movement along x, y and z axes, and rotational movement about those axes, corresponding to pitch, roll and yaw, respectively.

Further, in this example, the surface images provided are photographs of the sample. Preferably, the probe 12 is equipped with dual image acquisition capabilities so that the photographs of the sample can be obtained by the probe 12 simultaneously while the probe 12 scans the sample to obtain the volumetric images.

Figure 8:
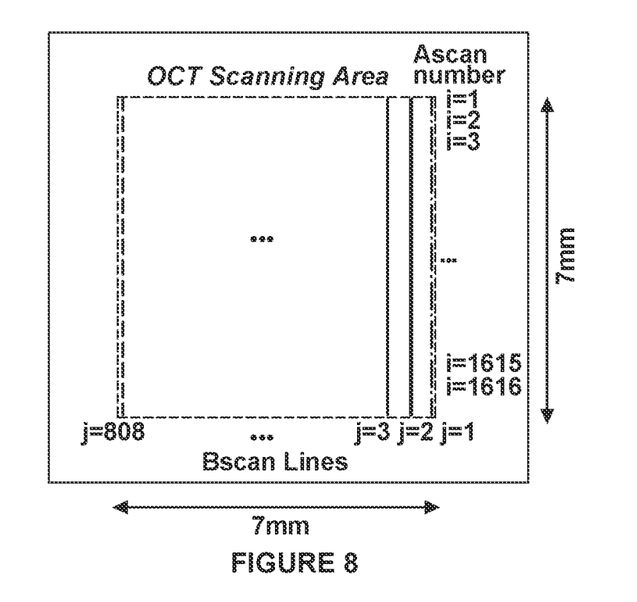
FIG. 8 shows a plot of scan lines for use in an embodiment of the invention.

The method 600 then comprises identifying 604 a change in the spatial position of the surface feature of each surface image. In this example, a particular en face plane (as opposed to the plane of a cross-sectional scan) of the OCT image is obtained. For each en face plane, a notional line of points referred to as a 'B-scan line' can be applied, as shown in FIG. 8. Each B-scan line composed of a line of points (i, j), where $j=1:j_{max}$ represents a B-scan line location along a first axis, and where $i=1:i_{max}$ corresponds to an A-scan location along a second axis perpendicular to the first axis. In this example, the first axis is a horizontal axis, and the second axis is a vertical axis. As a result, a set of coordinates (i, j) is provided for each en face plane.

The set of coordinates for each en face plane can then be transformed to a motion-corrected set of coordinates. This can be done, for example, by mapping each B-scan line according to the formula:

$$[i_{MC} j_{MC} 1] = [ij1] * P^{-1} * T_j P$$

In the formula above, $T_j$ is a transformation matrix derived from the surface image associated with the $j^{th}$ B-scan and the surface image taken associated with the first B-scan (or other reference B-scan). Matrices $P^{-1}$ and P are used to convert [i j 1] to and from a form the photograph or surface image pixel space to the OCT image surface voxel coordinate space.

Figure 9:
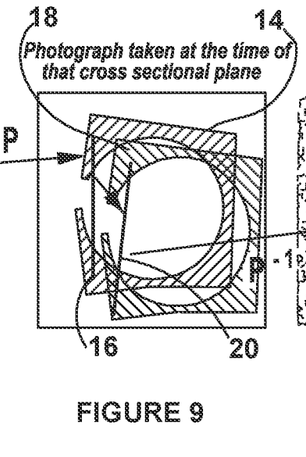
FIG. 9 shows surface images captured according to an embodiment of the present invention.

FIG. 9 shows a surface image 14 of the sample taken along a particular B-scan line (illustrated by line 16) superimposed with a reference surface image 18 previously acquired for a reference B-scan. Also superimposed onto the reference image 18 is a notional B-scan line 20 corresponding to the position of the B-scan line 16 when the image 18 was taken. As evident from the B-scan lines 16 and 20, at the time the image 14 was taken, the spatial position of the sample had changed since the reference image 14 was taken. A transformation matrix $T_j$ for each B-scan j can be derived by analysing the images 14 and 18, for example, using an affine image co-registration routine, which is capable of calculating how one image shifts with respect to another (e.g. translation, rotation and skew/dilation).

Thus, in this example, the step of identifying 604 a change in the spatial position of the surface feature may comprise:
identifying a position of a B-scan with respect to the surface image of the sample;
identifying a corresponding position of the B-scan with respect to the reference surface image of the sample; and
deriving a transformation matrix to transform the B-scan values (i, j) to corrected B-scan values ($i_{MC}$, $j_{MC}$).

Figure 10A:
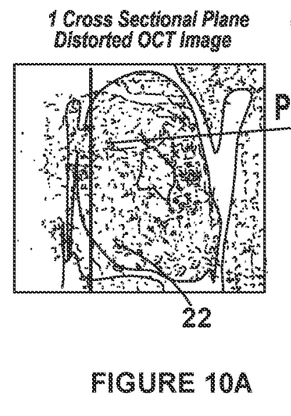
FIG. 10A shows a volumetric image to be correct according to an embodiment of the present invention.
Figure 10B:
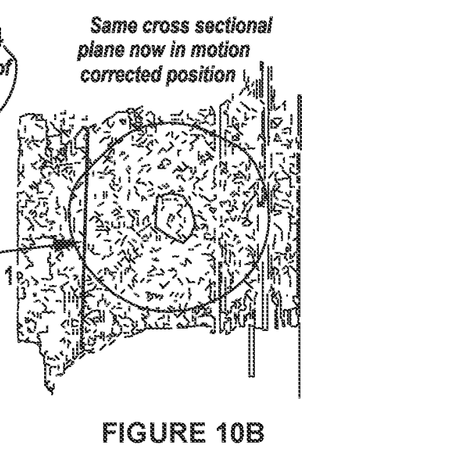
FIG. 10B shows a corrected volumetric image.

The plurality of depth images obtained by the probe 12 can then be processed 606 using the identified change of the spatial position, in order to obtain substantially corrected volumetric image. For example, FIG. 10A shows a skewed OCT image having a superimposed B-scan 22 corresponding to scan line 16 in the image 14 of the sample. Then, by mapping the original OCT image values with the transformed coordinates ($i_{MC}$, $j_{MC}$), a scatterplot can be generated to show the motion corrected en face OCT image, as shown in FIG. 10B. The scatterplot is thus constructed from corrected B-scan values ($i_{MC}$, $j_{MC}$) after transformation by $T_j$.

Figure 11:
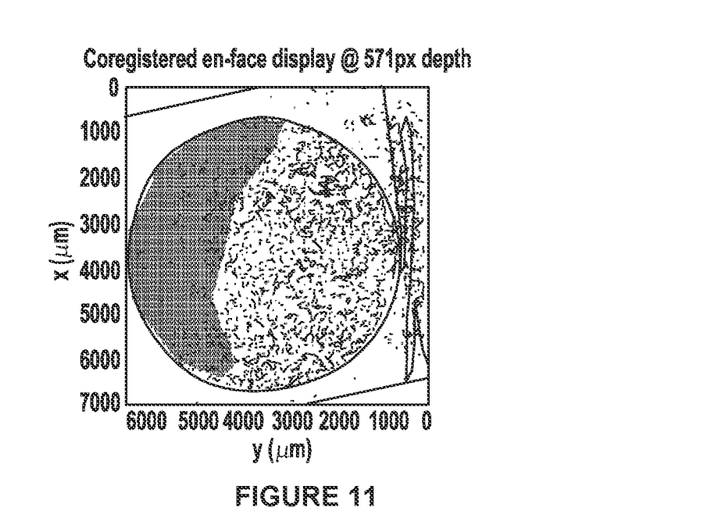
FIG. 11 shows the corrected volumetric image that has been processed further using interpolation.

However, depending on the nature of the relative movement between the scanner 12 and sample, the corrected image may have an irregular shape and/or there may be gaps in the image representing areas not scanned. Thus, to present the corrected image in a similar format to that usually obtained by OCT scans, missing portions of the corrected image may be interpolated. An example of a corrected OCT image with plot interpolations is shown in FIG. 11.

Assuming that pitch, yaw and z motion of the hand-held scanner 12 is negligible, the same motion correction transformations can be applied in the same way to every en face OCT plane in the acquired volumetric scan. It is envisaged that the transformation could however be extended to incorporate pitch, yaw and z motion.

It will be appreciated that an algorithm or appropriate computer programming software can be used to perform the method 600.

Figure 12:
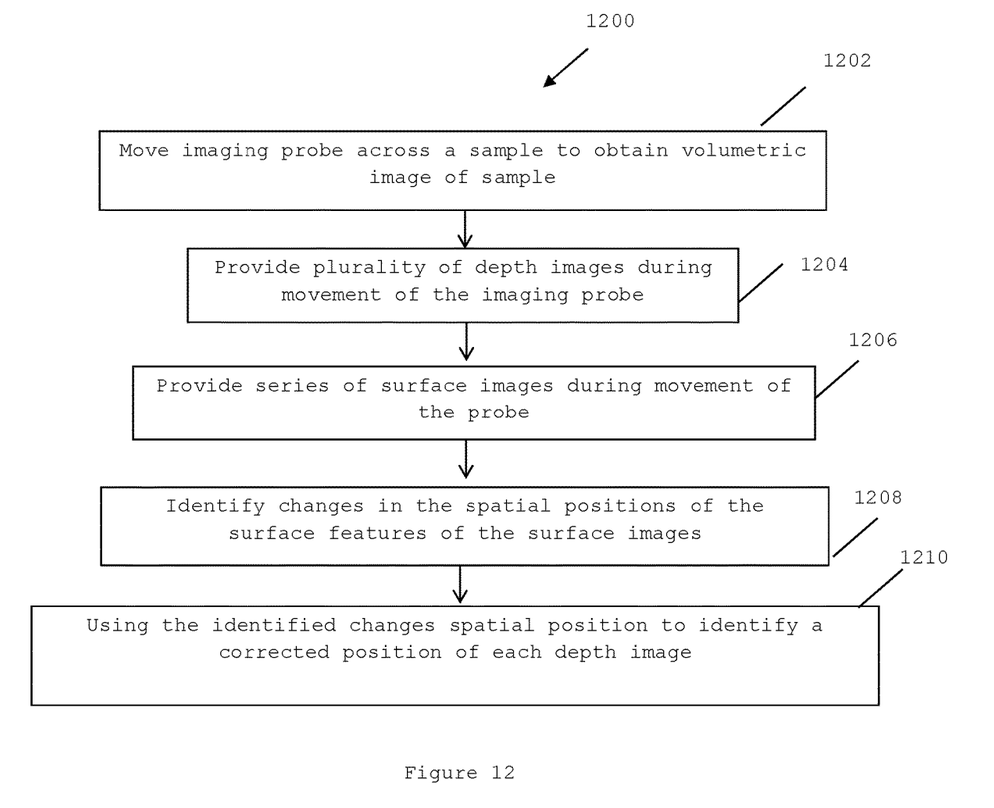
FIG. 12 is a flow diagram of a method according to another embodiment of the present invention.
Figure 13:
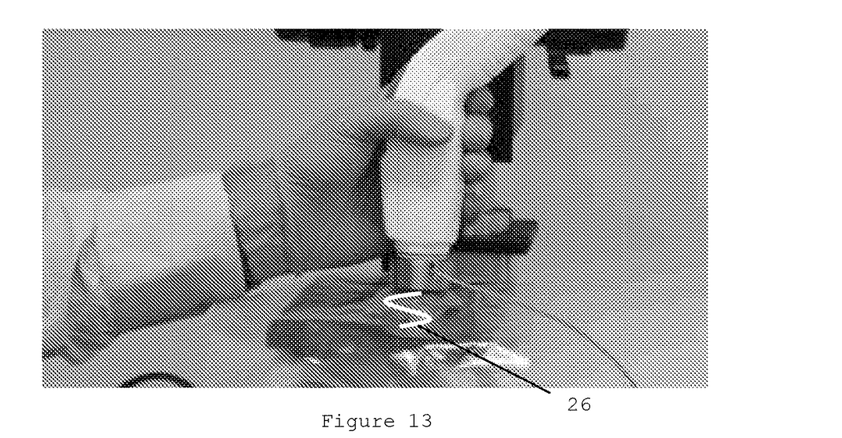
FIG. 13 shows a probe of a volumetric system, in use, that can be used in accordance with embodiments of the present invention.

FIG. 12 shows a flow diagram of a method 1200 of volumetric imaging of a sample according to an embodiment of the present invention. The method 1200 comprises moving an imaging probe of a volumetric imaging system and the sample relative to each other (step 1202). For example, the imaging probe may be arranged to obtain the depth images below a surface area A (such as 10×10 mm² for example). In order to obtain larger volumetric images (such as 2A or any other larger area size that is larger than a scanning range of the imaging probe), the imaging probe is then moved across the sample by a corresponding distance. The movement may be performed manually (using a handheld imaging probe) and consequently the movement may not be along a straight line and may also not cover exactly the required corresponding distance. This movement is illustrated in FIG. 13, which shows a path 26 across the sample as the probe 12 moves across the sample. The method 1200 then comprises providing a plurality of depth images during movement of the imaging probe across the sample (step 1204). For example, the imaging probe may be an OCT imaging probe 12 that is scanning the sample within an area of extension A during movement of the imaging probe across the sample.

The method 1200 then comprises providing a series of surface images during movement of the imaging probe 12 across the sample (step 1206). The method further comprises identifying a change in spatial position of surface features of each surface image (step 1208) and processing the plurality of depth images using the identified change in the spatial position to identify a corrected position of each depth image (step 1210) such that the relative movement is at least largely compensated using this processing step. In this case at least one surface image is provided for each depth image during movement of the imaging probe across the sample. The method then comprises generating at least one volumetric image for the expanded region (such as the region below a surface area of 2A). A person skilled in the art will understand that the above-described method may be used to generate volumetric images of any extension beyond a scanning extension of the imaging probe.

It will be understood to persons skilled in the art of the invention that many modifications may be made without departing from the spirit and scope of the invention.

For example, the method may be conducted using a volumetric imaging system other than OCT, such as an ultra-sound imaging system. The method may be conducted in-vivo or ex-vivo. In the case of the former, the method may be performed through an endoscope, such as a bronchoscope incorporated with an OCT imaging system and a digital camera.

Figure 14:
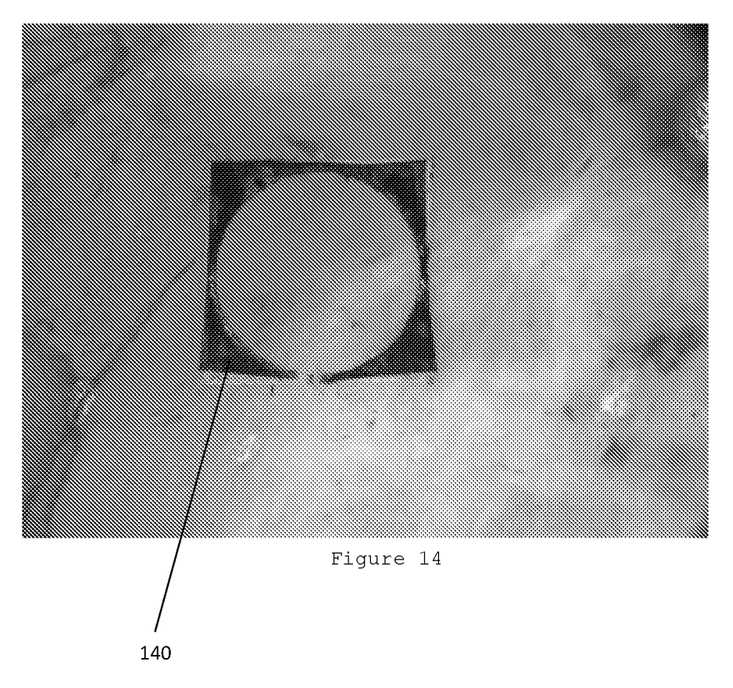
FIG. 14 shows a representation of a colour photograph of biological tissue captured in vivo.

As another example, instead of using a histology image 200, the surface image may be a photograph of the sample taken in vivo. An example of a colour photograph of a biological sample (breast cancer tissue) taken in vivo is shown in FIG. 14. FIG. 14 shows a fiducial marker 140 that is used to correct for motion artefacts in OCT images. In this example the fiducial marker 140 is formed from a rigid material placed on the tissue.

In an alternative embodiment a fiducial marker is provided in a different form. In this embodiment the fiducial marker is incorporated into a layered structure, such as a bi-layered structure having known mechanical properties. The bi-layered structure is used for indirect stress measurement of the tissue, which involves detecting a deformation of the layer positioned on the tissue in response to an applied load and then deducting mechanical or dynamic properties (such as stress) of the underlying tissue from a detected change in thickness of the layer in response to the applied load. Detecting a change in thickness of the bi-layered structure comprises in this example OCT imaging of interfaces of the bi-layered structure (for further details reference is being made to the applicant's co-pending U.S. patent application Ser. No. 15/023,663). In this embodiment the bi-layered structure enables the dual functions of stress measurement and motion correction. This is achieved by embedding the fiducial marker in a stiff layer that contacts the tissue and curing a second soft layer on top of the stiff layer. The soft layer has a stiffness similar to the tissue and is used for measuring stress. The reason for embedding the fiducial marker in a stiffer (which may comprise silicone) is to ensure that it is not deformed by the application of load. This would result in erroneous motion artefact correction. In a further variation of this embodiment the layer is a tri-layered structure, with the stiff layer incorporating the fiducial marker being sandwiched between two softer layers. One of the softer layer is positioned for contacting the tissue and is very thin (in the order of 100 um) and performs the function of allowing the tri-layered structure to adhere to the surface curvature of the tissue, ensuring a more even distribution of load within the tissue. This embodiment has the advantage that during a measurement that load can be applied evenly disturbing the application of the load, which may be caused by the marker shown 140 shown in FIG. 14, can be avoided.

As another example, the volumetric imaging system may be arranged for mechanical correction of the relative motion between the imaging system and the sample. Such mechanical correction may be substantially automatic and dynamic (i.e. substantially in real time, or with only minimal time delays), using a suitable control system with a feedback loop. In this embodiment, the step of processing the plurality of depth images of the region of interest using the surface image property may comprise controlling the volumetric imaging system to correct for an impact of the movement of the volumetric imaging system and the surface area of interest relative to each other. For example, during scanning of a sample using the probe 12 of the volumetric imaging system, a surface image may be taken (a "current surface image"). That surface image may be dynamically compared to a reference surface image taken of the sample prior to scanning. Then, using a shift/motion estimation algorithm, optical components of the probe 12 (such as mirrors) can be adjusted to counteract the image shift, such that the probe 12 captures a surface image as if there was less shift or no shift. The shift/motion algorithm could for example be based on an affine co-registration routine applied to the current and reference surface images. The same process can then be applied after such mechanical adjustment to counteract the image shift further, thus applying a feedback loop.

As another example, the step of processing the plurality of depth images may comprise correcting for deformation in the surface plane. For instance, if a motion artefact causes a shear force to deform surface features relative to each other, this could be detected during the processing step and corrected in the OCT image. In particular, if it is assumed that the deformation is linear elastic, an affine transformation could be applied to the deformed image and the resultant image compared to the original image. This comparison could be achieved using cross-correlation. The deformed image could be digitally "un-deformed" using the affine transformation until the deformed and original image match. The coordinates of the affine transformation that lead to this matching between the images could then be applied to the image volume to correct for the induced deformation.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

What is claimed is:

1. A method of volumetric imaging of biological tissue, the method comprising the steps of:
   providing a plurality of depth images of a region of interest of the biological tissue using a volumetric imaging system, the region of interest being below a surface area of interest of the biological tissue, each depth image being associated with a layer or slice of the region of interest and the plurality of depth images together forming a volumetric image of the region of interest;
   providing a surface image of the surface area of interest of the biological tissue;
   identifying a visible property of a surface portion of the surface area of interest using the surface image;
   identifying a portion of at least some of the depth images of the region of interest, the identified portion belonging to the same portion of the biological tissue as the surface portion having a tissue property that is different from a tissue property of surrounding tissue;
   associating the identified portion of at least some of the depth images with the visible property of a surface portion; and
   processing each of the plurality of depth images of the region of interest using the- visible property of a surface portion.

2. The method of claim 1, wherein the visible property is a colour of the surface portion.

3. The method of claim 1, wherein the surface image is acquired using a different imaging system to the volumetric imaging system.

4. The method of claim 1, comprising displaying the volumetric image with the same volume type having the surface image property.

5. The method of claim 1, wherein the imaging system is an OCT imaging system.

6. The method of claim 1, comprising determining a change in attenuation of an optical signal as a function of depth to determine a cross-sectional shape or depth extension of an identified portion.

7. The method of claim 1, comprising providing a series of surface images of the surface area of interest during movement of the volumetric imaging system and the surface area of interest relative to each other.

8. The method of claim 7, wherein the surface image property of the surface feature is a spatial position.

9. The method of claim 8, comprising identifying a change in the spatial position of the surface feature of each surface image and processing the plurality of depth images of the region of interest using the identified change of the spatial position to obtain a plurality of depth images of the region that are at least largely corrected for an impact of the movement of the volumetric imaging system and the surface area of the region of interest relative to each other.

10. The method of claim 1 comprising:
    moving at least a portion of the volumetric imaging system and the biological tissue relative to each other;
    providing a plurality of surface images during movement of the volumetric imaging system and the biological tissue relative to each other;
    identifying changes in spatial position of the surface features of the surface images and processing the plurality of depth images using the identified changes of the spatial positions to identify corrected spatial positions of the depth images; and
    generating at least one volumetric image using the depth images having the corrected spatial positions.

11. The method of claim 10 wherein the volumetric imaging system has a scanning range A and wherein the biological tissue and the volumetric scanning system are moved relative to each other such that a region B of the biological tissue is scanned and the region B has a surface extension that is larger than the scanning range A and wherein the at least one volumetric image is an image corresponding to the region B.

12. A method of volumetric imaging of a sample, the method comprising the steps of:
  providing a plurality of depth images using a volumetric imaging system during movement of a volumetric imaging system and the sample relative to each other, the volumetric imaging system being arranged for mechanical correction of the relative motion between the imaging system and the sample, each depth image being associated with a layer or slice of the region of interest and the plurality of depth images together forming a volumetric image of the region of interest;
  providing a plurality of surface images during movement of the volumetric imaging system and the sample relative to each other;
  identifying changes in spatial position of surface features of the surface images to obtain positional information; and
  controlling the volumetric imaging system to correct for an impact of the movement of the volumetric imaging system and the sample relative to each other using the obtained positional information;
  wherein the volumetric imaging system comprises a layer having known mechanical properties and incorporating a fiducial marker, the method further comprising: positioning the layer on the surface area of interest; applying a load to the region of interest and through the layer; detecting a deformation of the layer in response to the applied load; and using the fiducial marker for correcting for motion artefacts.

13. The method of claim 12 wherein the volumetric imaging system is arranged such that the movement correction can be performed mechanically using a suitable control system with a feedback loop.

14. The method of claim 12 wherein the layer comprises a layered structure within which the fiducial marker is positioned.

15. The method of claim 14 wherein the layered structure comprises layers having differing stiffness and wherein the fiducial marker is embedding in a layer having a stiffness that is greater than that of another layer of the layered structure.

16. The method of claim 15 wherein the layer in which the fiducial marker is positioned is in use located between the other layer having the lower stiffness and the region of interest and wherein the layered structure comprises a contact layer that has a stiffness that is lower than that of the layer in which the fiducial marker is embedded and wherein in use the layer in which the fiducial marker is embedded is positioned between two layers having the lower stiffness.

17. The method of claim 12 wherein the step of providing a plurality of depth images of a region of interest comprises OCT imaging and wherein the step of detecting a deformation of the layer in response to an applied load comprises OCT imaging of interfaces of the layer.

* * * * *